US00PP16006P2

(12) United States Plant Patent
Cain et al.

(10) Patent No.: US PP16,006 P2
(45) Date of Patent: Sep. 27, 2005

(54) PLUM TREE NAMED 'SUPLUMTWENTYSEVEN'

(50) Latin Name: *Prunus salicina*
Varietal Denomination: Suplumtwentyseven

(75) Inventors: David W. Cain, Bakersfield, CA (US); Terry A. Bacon, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 18 days.

(21) Appl. No.: 10/867,864

(22) Filed: Jun. 14, 2004

(51) Int. Cl.[7] ..... A01H 5/00
(52) U.S. Cl. ..... Plt./184

(58) Field of Search ..... Plt./184

(56) References Cited

U.S. PATENT DOCUMENTS

PP13,167 P2 11/2002 Mowrey et al. ..... Plt./184

*Primary Examiner*—Anne Marie Grunberg
(74) *Attorney, Agent, or Firm*—Knobbe, Martens, Olson & Bear, LLP

(57) ABSTRACT

A new and distinct plum tree variety, *Prunus salicina* 'Suplumtwentyseven' is disclosed. The new variety is characterized by consistent cropping of early-season, large-sized fruit (66 mm) in early June in Kern County. The fruit has golden-yellow flesh with ample juice. The skin is acidic, and has a smooth black finish.

1 Drawing Sheet

Latin name of the genus and species claimed: *Prunus salicina.*
Variety denomination: 'Suplumtwentyseven'.

BACKGROUND OF THE INVENTION

The present invention relates to a new and distinct variety of plum tree, herein after referred to by the cultivar name 'Suplumtwentyseven.' The new variety 'Suplumtwentyseven' originated by hybridization, being first hybridized by David Cain and selected by Terry Bacon. The new variety was first evaluated by Terry Bacon 75 near Wasco, Calif. in Kern County.

SUMMARY OF THE INVENTION

The new variety is characterized by possessing fruit with a smooth black finish and golden-yellow flesh. The plums have ample juice and approximately 15° brix with acidic skin. The new variety exhibits consistent cropping of early-season, relatively large-sized fruit (approximately 66 mm) during the same season as 'Black Beaut' (unpatented) in Kern County.

The seed parent of the new variety 'Suplumtwentyseven' is breeding selection '91P-060' (unpatented), and the pollen parent is cultivar 'Suplumtwentythree' (U.S. Plant Pat. No. 13,167). The parent varieties were first crossed in February 1997, with the date of planting of February 1998, and the date of first flowering being February 2000. The new plum variety was first asexually propagated by Terry Bacon near Wasco, Kern County, Calif. in 2001, by budding onto 'Nemared' (unpatented) rootstock.

The new variety 'Suplumtwentyseven' can be distinguished from its seed parent, '91P-060,' and its pollen parent, 'Suplumtwentythree,' by having yellow flesh while both parents have red flesh.

The new plum variety 'Suplumtwentyseven' may be distinguished from presently available cultivars in commerce by the following combination of characteristics: the new variety most nearly resembles the commercial plum, 'Black Amber' (unpatented) but ripens approximately 20 days earlier and has fruits that are larger (approximately 66 mm for 'Suplumtwentyseven' compared to approximately 58 mm for 'Black Amber'). The fruits of the new variety ripen approximately five days earlier than the variety 'Black Beaut.' The fruits of the new variety are also larger than 'Black Beaut' ('Black Beaut' fruits average approximately 58 mm).

The new variety 'Suplumtwentyseven' has been shown to maintain its distinguishing characteristics through successive asexual propagations by, for example, budding onto 'Nemared' (unpatented) rootstock.

BRIEF DESCRIPTION OF THE FIGURE

The accompanying color photographic illustration (FIG. 1) shows typical specimens of the foliage and fruit of the new plum variety 'Suplumtwentyseven.' The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED BOTANICAL DESCRIPTION OF THE INVENTION

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England.

The new variety 'Suplumtwentyseven' has not been observed under all possible environmental conditions. The phenotype may vary somewhat with variations in environment such as temperature, daylength, and light intensity, without, however, any variance in genotype.

The descriptive matter which follows pertains to five year old 'Suplumtwentyseven' plants grown primarily on 'Nemared' rootstock in the vicinity of Wasco, Kern County, Calif., during 2003, and is believed to apply to plants of the variety grown under similar conditions of soil and climate elsewhere.

TREE

General: (measurements taken on 5 year old tree unless otherwise noted).

*Tree size.*—Medium. Normal for most plum varieties. Reaches a height of approximately 3 meters including normal pruning.

*Tree vigor.*—Moderately vigorous, growth of approximately 1.5 to 2 meters in height the first growing season.

*Tree growth.*—Moderately upright.

*Tree productivity.*—Productive. Fruit set is usually two or more times desired amount for marketable size fruit. Thinning and spacing of fruit is necessary.

*Tree form.*—Vase formed.

*Bearer.*—Regular. No alternate bearing observed.

*Fertility.*—Self-sterile, pollinizer required.

*Tree canopy density.*—Dense. Pruning is required to open tree vase shape, allowing more sunlight to center of tree.

*Tree hardiness.*—Hardy in all fruit growing areas of California. Winter chilling requirement is approximately 600 hours at or below 7.2° C.

*Tree disease resistance/susceptibility.*—No specific testing for relative plant disease resistance/susceptibility has been designed. Under close observation in Wasco, Kern County, Calif., no particular plant/fruit disease resistance/susceptibility has been observed.

Trunk: (measurements at 30 cm above soil line).

*Trunk diameter.*—Approximately 9 cm. Varies with soil type, fertility, climatic conditions and cultural practices.

*Trunk texture.*—Medium-shaggy, increases with age of tree.

*Trunk color.*—Near Greyed-green 196A to Grey 201A on exposed areas, and near Greyed-orange 164B in recesses. Trunk color becomes darker with age.

Branches: (measurements at approximately 90 cm above soil line).

*Branch size.*—Diameter ranged from approximately 3 to 4 cm.

*Branch texture.*—Smooth on 1$^{st}$ year wood, increasing roughness with tree age.

*Branch color.*—Near Greyed-green 196A to Grey 201A on exposed areas, and near Greyed-orange 164B in recesses.

*Branch lenticels.*—Number: Numerous — varies from approximately 5 to approximately 9 per square centimeter. Lenticel number varies widely depending on environmental conditions and vigor of the plant. Color: Near Grey-brown 199D. Typical size: Approximately 4 mm in length and approximately 2 mm wide.

Flowering shoots: (data taken in July at midpoint of current-season growth).

*Flowering shoot size.*—Average diameter: approximately 5 mm.

*Flowering shoot color.*—Topside: Near Greyed-orange 165B with slight green background. Underside: Near Greyed-orange 165B with slight green background.

*Flowering shoot leaf buds.*—Shape: Ovoid. Width: Approximately 0.7 mm. Length: Approximately 0.9 mm. Color: Near Greyed-orange 166B.

*Flowering shoot flower buds.*—Shape: Ovoid. Width: Approximately 1 mm. Length: Approximately 1.8 mm. Color: Near Greyed-orange 166B.

LEAVES (data taken in July on fully expanded leaf at midpoint of current-season growth)

*Leaf size.*—Average length: approximately 96 mm.

*Average width.*—Approximately 48 mm.

*Leaf thickness.*—Medium.

*Leaf color.*—Upper surface: Near Green 137B. Lower surface: Near Green 138A.

*Leaf form.*—Broad obovate.

*Tip.*—Cuspidate.

*Base.*—Cuneate.

*Leaf margin.*—Irregularly and lightly crenate.

*Leaf venation.*—Pinately net veined.

*Leaf surface.*—Texture: smooth.

*Leaf petiole.*—Average length: Approximately 10 mm. Average diameter: Approximately 2 mm. Color: Near Yellow-green 147C.

*Leaf stipules.*—Number: 1 or 2 per leaf bud. Typical length: Approximately 7 mm.

*Leaf glands.*—Form: Usually eglandular, occasionally globose. Number: Varies from 0 to 2. Position: Opposite on upper portion of petiole. Average size: Approximately 0.5 mm by approximately 0.5 mm. Color: Near Greyed-orange 166B.

FLOWERS (fully opened)

General:

*Flower blooming period.*—First bloom: Approximately Feb. 23, 2003. Full bloom: Approximately Feb. 28, 2003.

*Flower size.*—Average diameter: Approximately 20 mm.

*Flower aroma.*—Very slight.

Flower peduncle:

*Length.*—Approximately 6 mm.

*Diameter.*—Approximately 1 mm.

*Color.*—Near Yellow-green 145A.

Flower petals:

*Number.*—5.

*Arrangement.*—Overlapping.

*Length.*—Approximately 10 mm.

*Diameter.*—Approximately 9 mm.

*Shape.*—Circular.

*Apex shape.*—Rounded.

*Base shape.*—Narrows at point of attachment.

*Color.*—White.

*Surface texture.*—Smooth.

*Margins.*—Smooth.

Flower sepals:

*Number.*—5.

*Length.*—Approximately 3 mm.

*Diameter.*—Approximately 2.5 mm.

*Shape.*—Elliptical with rounded tip and slightly serrated margin.

*Color.*—Near Yellow-green 145C.

*Surface texture.*—Smooth and irregularly rippled.

Flower stamens:
*Number.*—Approximately 22 to 28, average approximately 24.
*Average length.*—Approximately 7 mm.
*Filament color.*—White.
*Anther color.*—Near Greyed-orange 176A.
*Pollen color.*—Near Greyed-orange 176A.
Flower pistil:
*Number.*—Usually one, occasionally two.
*Average length.*—Approximately 8 mm.
*Ovary diameter.*—Approximately 1.5 mm.
*Pubescence.*—None.
*Stigma position.*—Stigma extends slightly below anthers.

FRUIT (data taken at firm-ripe on mature tree managed to obtain maximum quality)

General:
*Fruit harvest.*—Date of first pick: Approximately Jun. 5, 2003. Date of last pick: Approximately Jun. 15, 2003.
Fruit size:
*Length* (*stem end to apex*).—Approximately 62 mm.
*Diameter in line with suture plane.*—Approximately 66 mm.
*Diameter perpendicular to suture plane.*—Approximately 66 mm.
*Average weight.*—Approximately 152 gm.
Fruit form:
*Viewed from apex.*—Nearly round.
*Viewed from side, facing suture.*—Round-to-slightly flattened.
*Viewed from side, perpendicular to suture.*—Round to slightly flattened.
Fruit apex shape: Round to slightly flattened.
Fruit stem-end cavity depth: Shallow.
Fruit stem:
*Length.*—Approximately 9 mm.
*Diameter.*—Approximately 2 mm.
*Color.*—Near Green 143C.
Fruit skin:
*Thickness.*—Medium.
*Adherence to flesh.*—Tenacious.
*Surface texture.*—Smooth.
*Bloom.*—Moderate amount.
*Ground color.*—When visible, near Yellow-green 145A.
*Overcolor.*—Near Greyed-purple 187A, becoming black as fruit ripens.
*Taste.*—Acidic.
Fruit flesh:
*Ripens.*—Evenly.
*Texture.*—Fine, very firm, juicy.
*Fibers.*—Few, very short.
*Flavor.*—Tart-sweet.
*Brix.*—Approximately 15 degrees.
*Juice.*—Plentiful.
*Aroma.*—Slight.
*Color.*—Yellow-amber (near Yellow-orange 19C).
Fruit use: Dessert. Market, local and long distance.
Fruit shipping/keeping quality: Good. Holds well in cold storage for 6 weeks and maintains good firmness and eating quality. Minimal bruising and scarring in packing and shipping trials.
Stone: (Measurements taken on dried stones).
*Stone freeness.*—Clingstone.
*Stone size.*—Length: Approximately 22 mm. Diameter in line with suture plane: Approximately 19 mm. Diameter perpendicular to suture plane: Approximately 8 mm.
*Stone form* (*viewed from side*).—Rounded, asymmetrical.
*Stone form* (*viewed from stem end*).—Oval, nearly symmetrical.
*Stone base shape.*—Cuneate and flattened, retuse at stem attachment.
*Stone apex shape.*—Rounded with a small, dull point.
*Stone surface.*—Irregularly furrowed throughout. Lightly ridged toward base. Nearly smooth to lightly pitted throughout.
*Stone halves.*—Nearly equal.
*Stone ridges.*—1 ridge present on each side of the suture. The ridge is small and narrow beginning at the base and extending throughout the length of the stone.
*Stone outgrowing keel.*—Well developed.
*Stone tendency to split.*—None.
*Stone color.*—Near Greyed-orange 165C when dried.

What is claimed is:

1. A new and distinct variety of plum tree named 'Suplumtwentyseven' as herein illustrated and described.

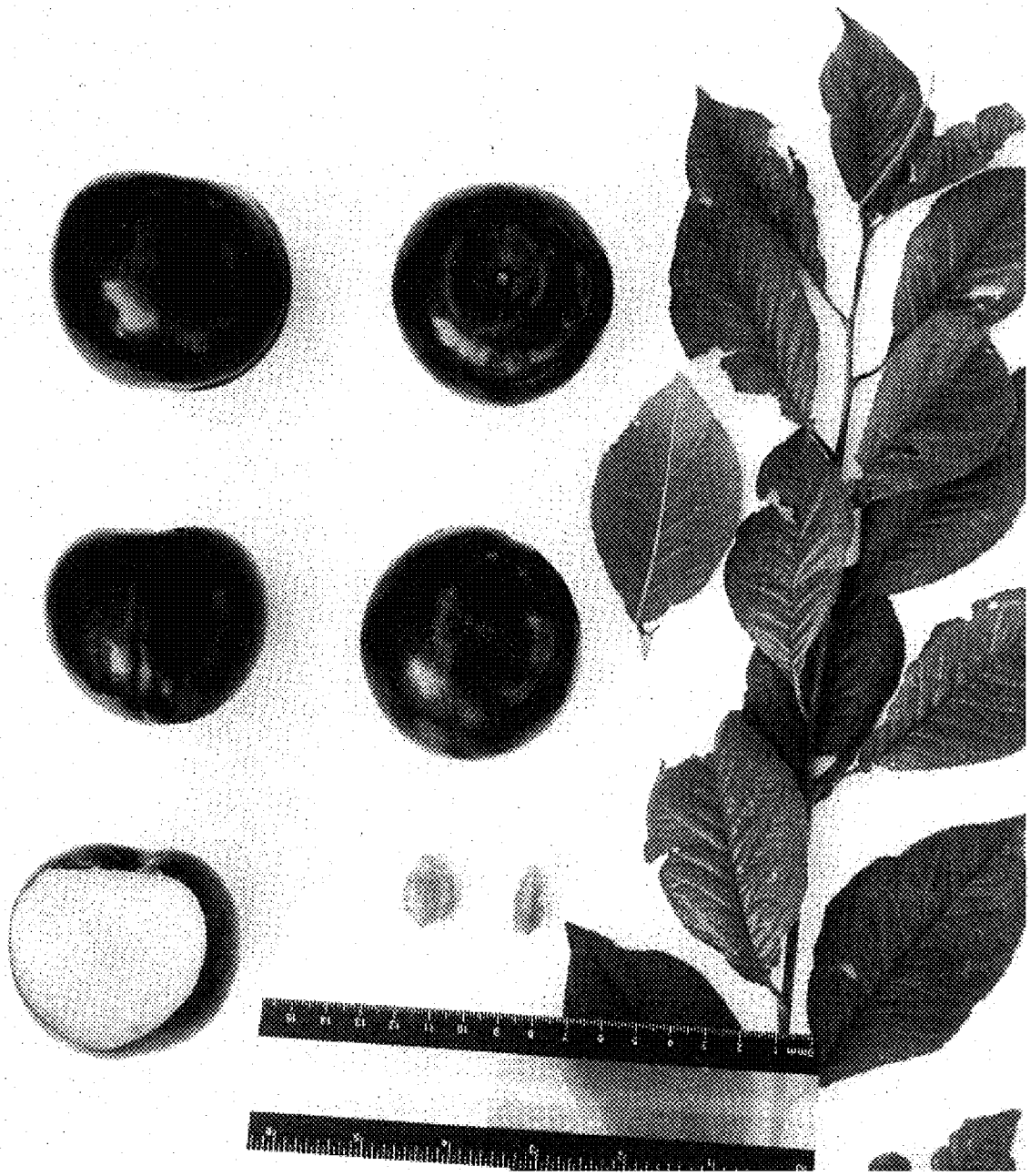

* * * * *